United States Patent [19]
Adair

[11] Patent Number: 5,325,845
[45] Date of Patent: Jul. 5, 1994

[54] STEERABLE SHEATH FOR USE WITH SELECTED REMOVABLE OPTICAL CATHETER

[76] Inventor: Edwin L. Adair, 317 Paragon Way, Castle Pines Village, Colo. 80104

[21] Appl. No.: 894,824

[22] Filed: Jun. 8, 1992

[51] Int. Cl.⁵ ............................................. A61B 1/00
[52] U.S. Cl. ............................................. 128/4; 604/95
[58] Field of Search ..................... 128/4, 6; 604/95; 138/120

[56] References Cited

U.S. PATENT DOCUMENTS

| | | | |
|---|---|---|---|
| 2,975,785 | 3/1961 | Sheldon . | |
| 3,266,059 | 8/1966 | Stelle . | |
| 3,572,325 | 3/1971 | Bazell et al. . | |
| 3,605,725 | 9/1971 | Bentov . | |
| 3,610,231 | 10/1971 | Takahashi . | |
| 3,799,151 | 3/1974 | Fukaumi et al. . | |
| 4,499,895 | 2/1985 | Takayama . | |
| 4,530,568 | 7/1985 | Haduch et al. | 128/6 X |
| 4,659,195 | 4/1987 | D'Amelio et al. | 128/4 X |
| 4,696,544 | 9/1987 | Costella | 128/6 X |
| 4,753,223 | 6/1988 | Bremer . | |
| 4,758,222 | 7/1988 | McCoy | 128/6 X |
| 4,784,117 | 11/1988 | Miyazaki | 128/4 |
| 4,815,450 | 3/1989 | Patel | 128/4 X |
| 4,834,069 | 7/1989 | Umeda . | |
| 4,896,941 | 1/1990 | Hiyashi et al. | 128/6 X |
| 4,998,916 | 3/1991 | Hammerslag et al. . | |
| 5,083,549 | 1/1992 | Cho et al. | 128/4 X |
| 5,116,317 | 5/1992 | Carson, Jr. et al. | 128/6 X |
| 5,125,395 | 6/1992 | Adair | 128/4 |

FOREIGN PATENT DOCUMENTS

| | | | |
|---|---|---|---|
| 0114224 | 4/1990 | Japan | 128/4 |
| 9111213 | 8/1991 | World Int. Prop. O. | 604/95 |

*Primary Examiner*—Richard J. Apley
*Assistant Examiner*—Karen Jalbert
*Attorney, Agent, or Firm*—Fields, Lewis, Pittenger, Rost & Smith

[57] ABSTRACT

A steerable sheath for use with one of several optical catheters is provided to be positioned in a passageway leading to a body cavity of a patient for observation and/or treatment. The apparatus includes an elongated, deformable, hollow body having a distal end and a proximal end. An optical catheter is removably extendable through the body and has a distal end which is alignable with the distal end of the body and a proximal end extendable outwardly beyond the proximal end of the body. An articulatable hollow, cylindrical member is provided within the sheath body at the distal end thereof and extends along the sheath body for a short distance toward the proximal end. A first generally cylindrical yoke is pivotally mounted about an axis at the proximal end of the sheath body. The proximal ends of a first pair of wires which extend longitudinally within the sheath body from the distal end thereof to the proximal end are attached to the first yoke and offset 90° from the first yoke axis. A first knob is connected to the first yoke for rotating it back and forth about the first yoke axis to alternately push and pull the first pair of wires to steer the cylindrical member in an appropriate direction. A method is also contemplated using the apparatus in conducting an investigation and/or operative procedure.

3 Claims, 3 Drawing Sheets

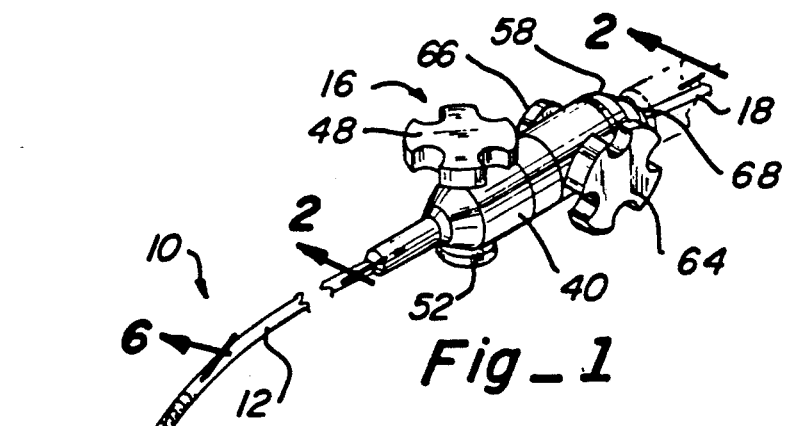
Fig_1
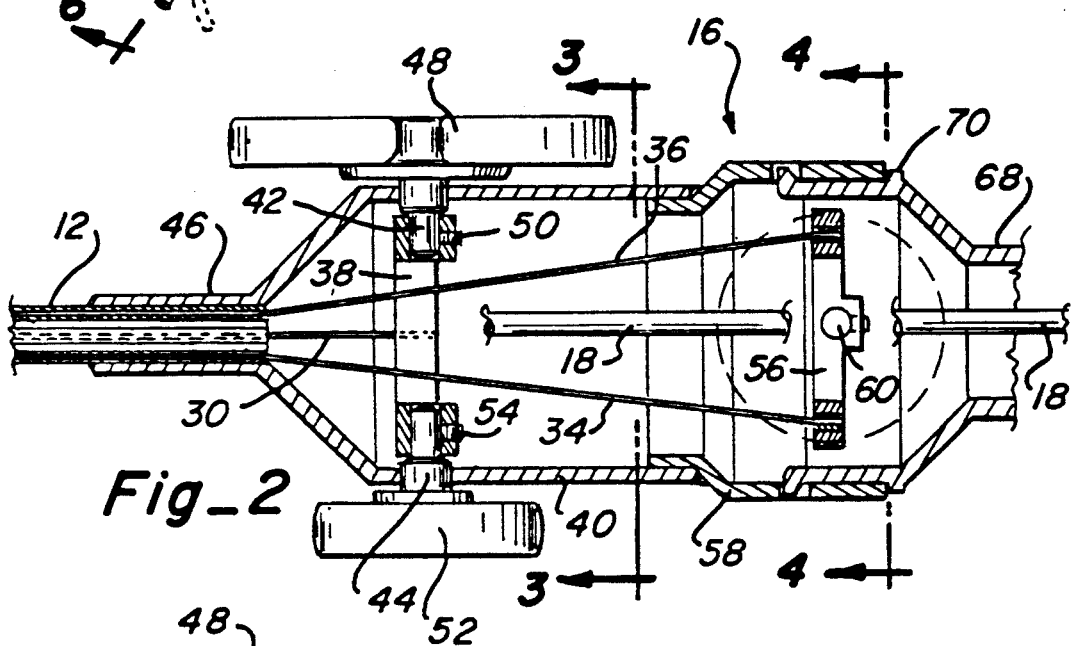
Fig_2
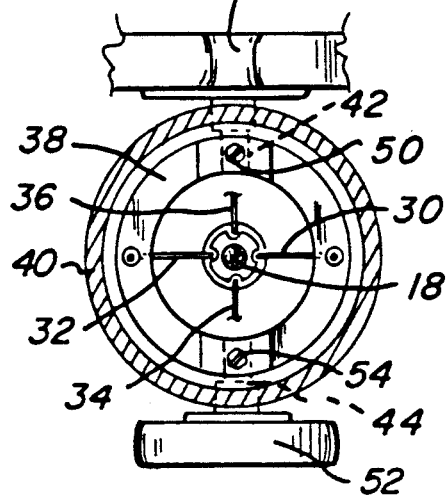
Fig_3
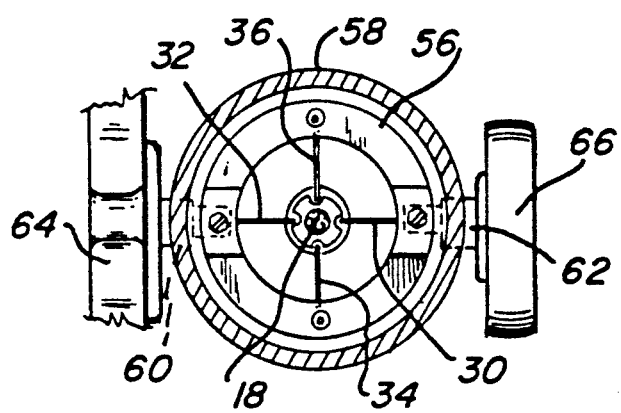
Fig_4

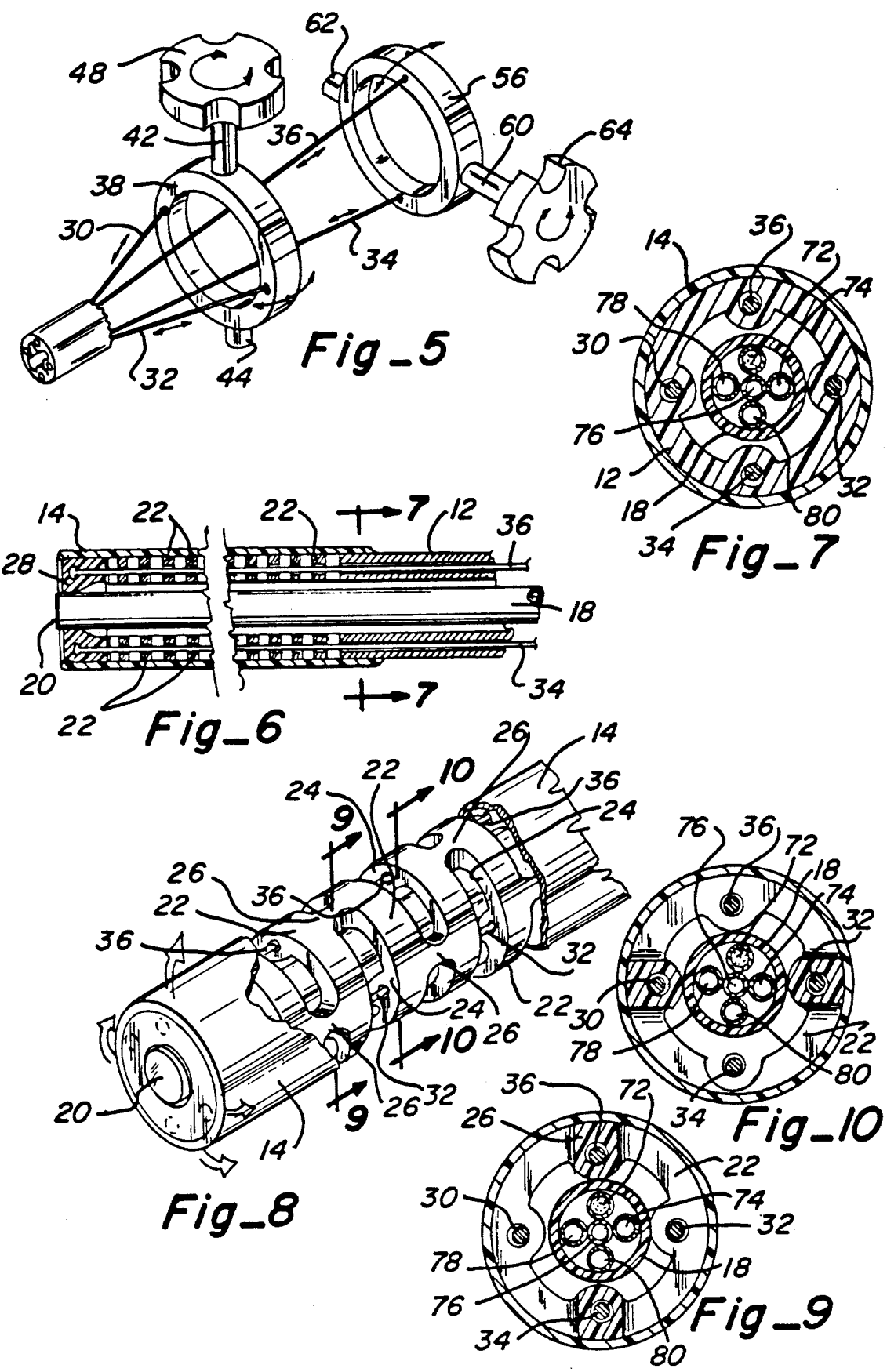

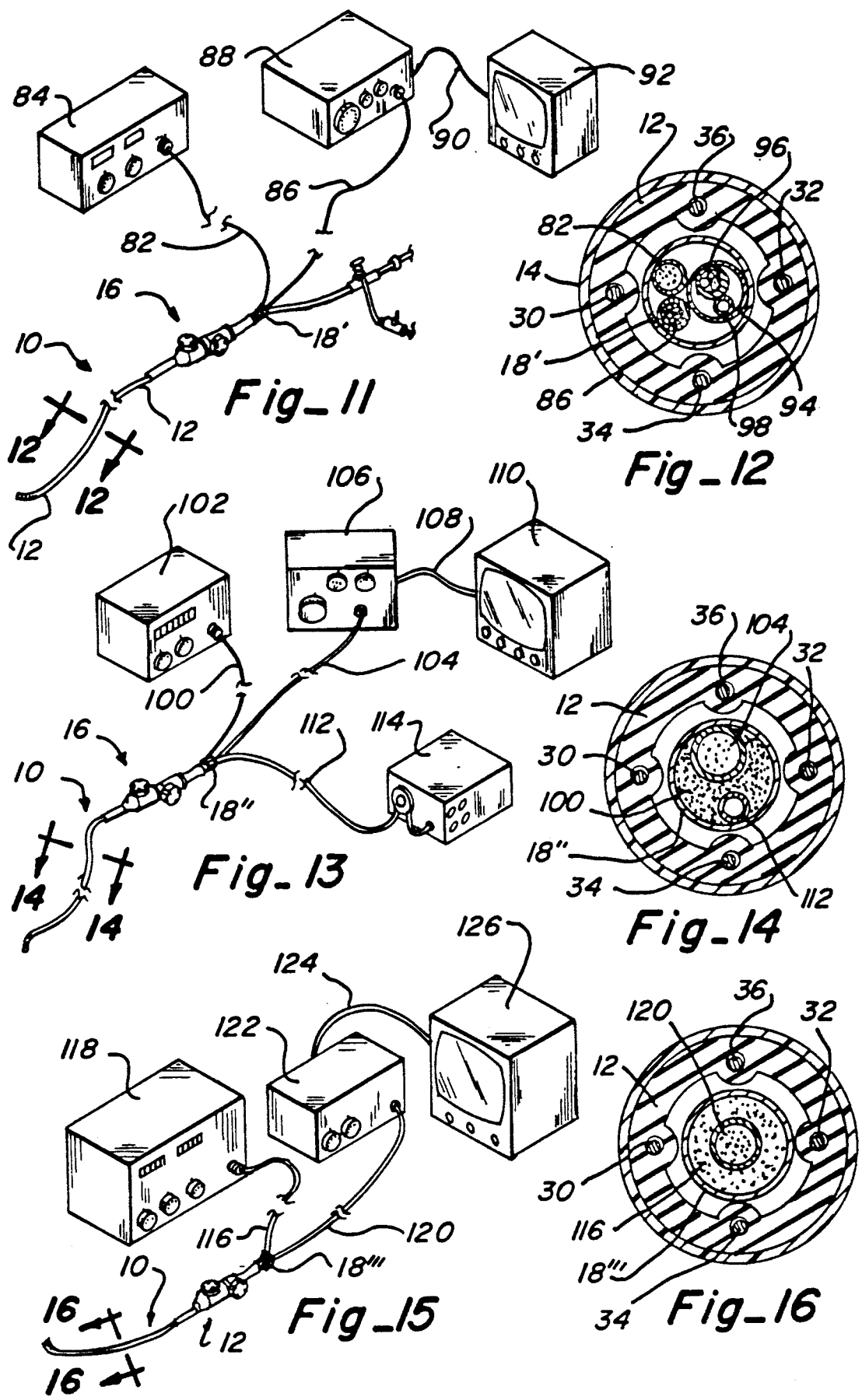

STEERABLE SHEATH FOR USE WITH SELECTED REMOVABLE OPTICAL CATHETER

TECHNICAL FIELD

This invention relates to a steerable sheath and more particularly to such a steerable sheath for use with one of several selected removable optical catheters wherein means is provided for bending the distal end of the sheath and the selected optical catheter in any desired direction for observation and/or treatment.

BACKGROUND ART

Most fiber optic endoscopes on the market today are made in a conventional manner wherein they include an elongated body or shaft containing both image fibers and light carrying fibers. The endoscope may also have additional passageways for irrigation and/or for conducting operative or investigative procedures. Sometimes it also will be provided with a steering mechanism for pointing the distal end thereof. Most optical endoscopes are configured in a shape to do one specific examination. For example, one may be a flexible cystourethroscope for examination of the lower genitourinary tract. Another may be a bronchoscope for looking into the respiratory tract. Still another may be a flexible hysteroscope for looking into the uterus. Once any of these devices is manufactured, it is locked into that configuration and generally can only be used for the purpose for which it was constructed. In other words, it is not adaptable for other types of examinations. An exception to this is that in rare instances one may use a flexible hysteroscope for looking into the bladder. This is done only because the regular scope is broken or unavailable, or done by mistake. There also is a device now available for looking the nasal sinuses. This is a small flexible scope which has an eyepiece, a steering mechanism for changing direction of the device to allow its manipulation into a sinus opening and a light connector. However, it cannot be used for any other purpose.

Because of the necessity for providing a variety of types and styles of endoscopes, the cost invested in endoscopes can be quite high, inasmuch as they are not interchangeable.

U.S. Pat. No. 2,975,785 to Sheldon discloses an endoscope with spaced segments interconnected by two pairs of cables located on opposite sides of the segments. Each pair of cables has distal ends which extend around pulleys mounted on a common shaft which is attached to a handle for rotating the shaft. The rotation of the shaft will cause one of the pairs of cables to be shortened and the other to be lengthened so as to bend the distal end of the endoscope in the desired direction. With the two pairs of cables and control means, the endoscope can be bent in any desired direction.

U.S. Pat. No. 3,266,059 to Stelle discloses a prestressed, articulated joint having pivotal segments which are moved by cables. Associated springs prestress the joint.

U.S. Pat. No. 3,572,325 to Bazell et al., discloses an endoscope with spaced annular segments having control cables extending from the distal end to the proximal end where the cables are connected to a wobble plate which is pivoted to lengthen and shorten the cables to create appropriate bending of the endoscope.

U.S. Pat. No. 3,605,725 to Bentoy discloses a non-circular catheter having a flexible catheter tip with control members extending along the length of the catheter for controlling the angle of the tip. The control means extend from the proximal end of the catheter and are designed for rapid connection to a control mechanism.

U.S. Pat. No. 3,610,231 to Takahashi discloses an endoscope with a stiff central stay and cables which connect to rotatable elements at the proximal end of the endoscope to alternately lengthen and shorten the cables to deflect the distal end of the endoscope in any direction desired. Again, two pairs of cables are provided which are lengthened and shortened together as an appropriate control mechanism is manipulated.

U.S. Pat. No. 3,799,151 to Fukaumi et al., discloses an endoscope with sections that are pivoted together in series and have wires which can be lengthened and shortened for manipulation of the endoscope to cause bending in any desired direction.

U.S. Pat. No. 4,499,895 to Takayama discloses an endoscope with wires that are lengthened and shortened by means of a motor which rotates in response to movement of a control lever.

U.S. Pat. No. 4,753,223 to Brewer discloses a flexible catheter having a plurality of electrical conductors wrapped about an inner tubular body. An insulating layer surrounds the conductors. Rigid non-conductive rings are adhesively secured at axially spaced locations along the distal end of the probe. A plurality of shape memory titanium-nickel wires extend between adjacent pairs of rings and are electrically connected to a control device and power source. Low current pulses are selectively provided by the control device through one or more of the wires to effect contraction of the heater wires to thereby cause the distal end of the probe to bend in a desired direction.

U.S. Pat. No. 4,834,069 to Umeda discloses a guidable endoscope made up of a plurality of articulated tubular members which have passage means for guide wires along the inner portion thereof through which manipulating wires extend for bending the endoscope in a desired direction and position.

U.S. Pat. No. 4,998,916 to Hammerslag et al. discloses a steerable guide wire or catheter for coronary angioplasty applications. A floppy steerable tip is provided on a steering region at the distal end of the implement and a control device at the proximal end, connected by means of a plurality of axially movable deflection wires, extends through the implement. Manipulation of a control permits deflection of the steering region through a full 360° range of motion about the axis of the catheter.

U.S. Pat. No. 5,005,558 to Aomori discloses an endoscope which has an operating body formed as a flexible insertion tube having a bendable tube part with wires for bending the bending tube part by operating a control knob. The bending tube part includes ring link members which are tubular and are connected by flexible connections at upper and lower or left and right sides thereof, alternately to connect the ring link members with one another in series.

Although each of the previously described devices are suitable for their intended purpose, each is rather complex and not of sufficiently simple construction so as to be disposable after each use. In other words, these devices are of unitary construction, housing both the catheter and steering mechanism in one apparatus, and are very expensive. As pointed out above, separate endoscopic devices must be provided for different procedures. Thus, a very expensive endoscope with a steerable device is required for each endoscopic procedure creating a very high cost in maintaining separate endoscopic instruments for all of the various uses contemplated. Also, since the sheath is relatively inexpensive compared to the cost of many catheters, if the sheath cannot be adequately sterilized to prevent the transfer of disease from one patient to another, it can be thrown away after each use.

DISCLOSURE OF THE INVENTION

The present invention relates to a steerable sheath for use with one of several optical catheters to be positioned in a passageway leading to a body cavity of a patient for observation and/or treatment. The apparatus includes an elongated, deformable, hollow body having a distal end and a proximal end. An optical catheter is removably extendable through the body and has a distal end which is alignable with the distal end of the body and a proximal end extendable outwardly beyond the proximal end of the body. An articulatable hollow, cylindrical member is provided within the sheath body at the distal end thereof and extends along the sheath body for a short distance toward the proximal end. A first generally cylindrical yoke is pivotally mounted about a first axis at the proximal end of the sheath body. The proximal ends of a first pair of wires which extend longitudinally within the sheath body from the distal end thereof to the proximal end are attached to the first yoke and offset 90° from the first yoke axis. A first knob is connected to the first yoke for rotating it back and forth about the first yoke axis to alternately push and pull the first pair of wires to steer the cylindrical member in an appropriate direction.

The apparatus can include a second pair of wires extending longitudinally within the sheath body from the distal end thereof to the proximal end, the second pair of wires having a distal end connected to opposite sides of the distal end of the articulatable member and offset 90° from the first pair of wires. A second generally cylindrical yoke can be pivotally mounted about an axis offset 90° from the first yoke axis and mounted on the proximal side of the first yoke. The proximal ends of the second pair of wires can be attached to opposite sides of the second yoke offset 90° from the second yoke axis. A second knob is connected to the second yoke for rotating it back and forth about the second yoke axis to alternately push and pull a second pair of wires to provide further steering control of the cylindrical member.

The articulatable member can comprise longitudinally spaced rigid segments and a pair of hinges interconnecting opposite sides of adjacent segments and offset 90° from the first pair of wires and a second pair of hinges interconnecting opposite sides of the other pairs of segments and offset 90° from the second pair of wires. The second pair of wires can be arranged to pass through the center portion of the first yoke. In addition, the articulatable member can include a sleeve connected to the most proximal of the segments and extending within the sheath body toward the proximal end. Four passageways are provided equally spaced around the sleeve for slidably receiving and guiding the first and second pairs of wires.

It can be seen that a very simple construction is provided, resulting in the steerable sheath for one of several selected removable optical catheters as contemplated in the present invention. It is inexpensive in comparison to the cost of the catheter and should it be desirable to use the sheath only for one operative procedure to prevent disease or contamination transfer to another patient, the expensive catheter can merely be withdrawn from the sheath after the procedure and the sheath can be thrown away.

With any of the apparatus described above, a unique method of carrying out an investigative and/or operative procedure is contemplated. The method includes the steps of providing a flexible, elongated sheath having means therein for steering the distal end thereof; inserting a flexible optical catheter, having a distal end, through the center of the sheath and the steering means so that the distal end of the catheter is aligned with the distal end of the sheath; inserting the sheath with the catheter in place therein into a passageway in the body of a patient; steering the distal end to a desired position with the steering means; conducting an investigative and/or operative procedure when the sheath has been steered to the desired position; straightening the sheath with the steering means after the investigative and/or operative procedure has been completed; removing the used sheath with the catheter in place therein from the passageway in the body of the patient; removing the catheter from the used sheath; and disposing of the used sheath. The method also contemplates the additional step of inserting the catheter into a new sheath with the distal end of the catheter aligned with the distal end of the new sheath and repeating the proceeding steps.

Additional advantages of this invention will become apparent from the description which follows, taken in conjunction with the accompanying drawings.

BRIEF DESCRIPTION OF THE DRAWINGS

FIG. 1 is a fragmentary perspective view of a steerable sheath constructed in accordance with this invention and showing a removable catheter therein;

FIG. 2 is an enlarged horizontal section, taken along line 2—2 of FIG. 1 showing details of the control mechanism for manipulating the sheath;

FIG. 3 is a vertical section, taken along line 3—3 of FIG. 2 showing details of a first yoke for operating a first pair of guide wires;

FIG. 4 is a vertical section, taken along line 4—4 of FIG. 2, showing details of a second yoke for manipulating a second pair of guide wires;

FIG. 5 is a perspective view of the first and second yoke and the manner in which they are connected to and control the guide wires;

FIG. 6 is a fragmentary horizontal section, taken along line 6—6 of FIG. 1, showing the distal end of the deformable and removable sheath;

FIG. 7 is an enlarged, vertical section, taken along line 7—7 of FIG. 6, showing further details of the invention;

FIG. 8 is an enlarged perspective view of the distal end of the sheath of FIG. 1 with the outer layer partially removed for clarity of illustration of the hinge structure;

FIG. 9 is a vertical section, taken along line 9—9 of FIG. 8, showing further details of the hinge structure;

FIG. 10 is a vertical section, taken along line 10—10 of FIG. 8, showing additional details of the hinge structure;

FIG. 11 is a perspective view of the steerable sheath of this invention in use with an alternative replaceable endoscope wherein a small image bundle, a small number of light fibers and a large channel for passing instruments and fluid is provided;

FIG. 12 is a greatly enlarged cross-section taken along line 12—12 of FIG. 11, showing further details of this replaceable endoscope;

FIG. 13 is a perspective view, similar to FIG. 11, but showing a replaceable endoscope having a large image bundle, a large number of light fibers and a small channel only for fluid, but not instruments;

FIG. 14 is a greatly enlarged cross-section, taken along line 14—14 of FIG. 13, showing the details of this replaceable endoscope;

FIG. 15 is a perspective view similar to FIGS. 11 and 13, but showing an endoscope with an image and light bundle and no operating channels; and FIG. 16 is a greatly enlarged cross-section, taken along line 16—16 of FIG. 15, showing further details of this replaceable endoscope.

BEST MODE FOR CARRYING OUT THE INVENTION

In accordance with this invention, a steerable sheath 10 is provided which has a flexible body 12 with a distal end within a sleeve 14 and a proximal end connected to a steering mechanism 16, which will be more fully described below. A removable catheter 18 is extendable through steering mechanism 16 and sheath body 12 and has a distal end 20 which is aligned with the distal end of the sheath after insertion therein, as best seen in FIG. 6. The distal end of body 12 has articulated circular segments 22 which are protected by sleeve 14, as best seen in FIGS. 6 and 8. The articulated segments 22 can be formed from a solid cylindrical member which has slots 24 cut in the side wall to form the segments and where a bridge portion 26 is left remaining on opposite sides to form flexible hinges. Conveniently, the hinges for every other pair of segments is offset 90° from the hinges for the alternate segments. Thus, bending can be accomplished in opposite directions along perpendicular planes passing through the device. The most distal segment is similarly hinged to a ring 28 to which are anchored a distal end of a first pair of control wires 30 and 32 and a second pair of control wires 34 and 36. The guide wires extend through the hinges 26, as shown in and through the interior of body 12 to the proximal end, as shown in FIG. 2. The wires 30 and 32 extend beyond the proximal end to a first yoke 38 which is mounted for rotation about a vertical axis in housing 40 about upper and lower pins 42 and 44, respectively. The housing 40 includes a distal sleeve 46 which extends over and is securely attached, as by gluing or heat sealing to sheath body 12. A control knob is connected to upper shaft 42 for rotating the yoke about its pivot so as to extend wire 30 while retracting wire 32, and vice versa, to cause movement of the distal end of the sheath 10 in opposite directions. Conveniently, knob 48 is held in position within a socket in yoke 38 by set screw 50. Similarly, a smaller knob or nut 52 is formed inwardly with pivot pin 44 and is held in place in a socket in yoke 38 by a set screw 54.

The second set of guide wires 34 and 36 extend through the center of first yoke 38 and are anchored to the upper and lower sides of a second yoke 56 which is pivotally mounted in a housing 58 which is telescopically received in housing 40, as shown in FIG. 2. Second yoke 56 pivots about pivot pins 60 and 62 within housing 58 which are offset 90° from pivot pins 42 and 44. A control knob 64 is connected to pin 60 for rotating yoke 56 about its axis so as to lengthen wire 36 when shortening wire 34 and vice versa to cause pivotal movement of sheath 10 in the opposite directions. Thus, by controlling knobs 48 and 60, the distal end of the sheath can be steering in any desired direction. The mounting for shaft 60 and 62 in housing 58 is identical to that shown in FIG. 2 for the shaft and housing for yoke 38. In this regard, as best seen in FIG. 4, pivot pin 62 is received in a nut 66 positioned outwardly of housing 58.

As seen in FIGS. 1 and 2, the catheter 18 is extendable through a sleeve 68 having a lure lock 70 on the end thereof which releasably attaches to housing 58 so as to properly orient the position of the catheter within sheath 10 so that an image projected from the site under investigation at the end of the distal end of the sheath as properly oriented on a video screen (not shown) which forms a part of a console (not shown), such as the type shown in U.S. Pat. No. 4,589,404. The catheter, as best seen in FIGS. 7, 9 and 10, can be provided with several passageways for different purposes. For example, laser fiber bundle 72 can be provided for lithotripsy. A passageway 74 can be provided for irrigation. A fiber optic bundle 76 can include one or more optic fibers for transmitting light from the console to the distal end of the catheter to illuminate the site under investigation. In addition, bundle 76 will contain coherent fibers to project an image to the video screen associated with the console. An irrigation passage 78 can also be provided, if needed. Finally, a fourth channel 80 can be provided for providing surgical procedures, such as a biopsy.

Alternative catheter configurations which can be used within sheath 10 are shown in FIGS. 11-16. In this regard, FIGS. 11 and 12 show an optical catheter 18' which has a small fiber bundle 82 for transmitting light from a light source 84 to the site under investigation. The image is reflected back through optical bundle 86 to a video camera or image processing device 88. This device is connected by a cable 90 to a video monitor 92 which displays an image from the viewing site. As best seen in FIG. 12, a channel 94 is provided having a passageway 96 for insertion and removal of instruments and a fluid passageway 98.

Another catheter 18" is illustrated in FIGS. 13 and 14 which has a large fiber bundle 100 which provides light from a light source 102 to the site under investigation. An optical bundle 104 transmits an image to an image processor 106 connected by means of a cable 108 to a video monitor 110. A fluid channel 112 is provided within catheter 18" and supplies fluid to the operative or investigative site from a fluid source 114.

A further catheter 18''' is shown in FIGS. 15 and 16 which is useable within sheath 10. Catheter 18''' has a fiber bundle 116 which provides light from a light source 118 to the site under investigation. The image at the site is reflected through optical bundle 120 to a video camera or image processor 122 connected by means of a cable 124 to a video monitor 126. With any of the apparatus described above, a unique method of carrying out an investigative and/or operative procedure is contemplated. The method includes the steps of providing a flexible, elongated sheath having means therein for steering the distal end thereof; inserting a flexible optical catheter, having a distal end, through the center of the sheath and the steering means so that the distal end of the catheter is aligned with the distal end of the sheath; inserting the sheath with the catheter in place therein into a passageway in the body of a patient; steering the distal end to a desired position with the steering means; conducting an investigative and/or operative procedure when the sheath has been steered to the desired position; straightening the sheath with the steering means after the investigative and/or operative procedure has been completed; removing the used sheath with the catheter in place therein from the passageway in the body of the patient; removing the catheter from the used sheath; and disposing of the used sheath. The method also contemplates the additional step of inserting the catheter into a new sheath with the distal end of the catheter aligned with the distal end of the new sheath and repeating the proceeding steps.

From the foregoing, the advantages of this invention are readily apparent. A sheath of very simple construction has been provided which allows for a steerable distal end which is operated by pairs of wires connected to yokes which can be pivoted about axes which are rotated 90° from each other to provide very precise control in every direction. It is designed to removably receive any one of a selected number of catheters. Each of these catheters can be removed after use of the sheath and replaced with a catheter designed for a different purpose or for a different procedure. If it is felt desirable or necessary, the sheath may be disposed of after a particular procedure to minimize the chance of infection or contamination of a subsequent patient without disposing of an expensive catheter.

This invention has been described in detail with reference to a particular embodiment thereof, but it will be understood that various other modifications can be effected within the spirit and scope of this invention.

I claim:

1. A medical apparatus having a steerable and removable sterile sheath which is disposable after a single use, for use with an optical catheter which has no steering mechanism, wherein said sheath with a catheter therein is positionable in a passageway leading to a body cavity of a patient for observation and/or treatment, said apparatus comprising:

an elongated, bendable, hollow body having a distal end, a proximal end and a central channel extending from said proximal end to said distal end for receiving an optical catheter having a distal end alignable with said distal end of said body and a proximal end extendable outwardly beyond said proximal end of said body, the catheter being conformable to the shape and movement of said body;

an articulatable hollow, cylindrical member within said sheath body at the distal end thereof having a distal end and extending along said sheath body for a short distance toward said proximal end;

activatable means extending within said sheath body from a connection to said articulatable member to said proximal end of said sheath;

control means connected to said activatable means at said proximal end of said sheath for selectively deflecting said articulatable member and said distal end of said sheath body to bend the distal end of the removable catheter therein a flexible and removable non-steerable catheter having a longitudinal body having a distal end, said distal end of said catheter body being aligned with said distal end of said sheath so that said distal end of said catheter bends with said distal end of said sheath when said distal end of said sheath is deflected by said control means;

a fiber bundle extending through said longitudinal body for providing light to the site; and an optic bundle extending through said longitudinal body for transmitting an image from the site to a viewing device.

2. A medical apparatus having a steerable and disposable sterile medical sheath for use with one of several selected removable and flexible non-steerable medical optical catheters wherein said sheath with one of the catheters therein is positionable in a passageway leading to an observation and/or treatment site of a patient, said sheath comprising:

an elongated, bendable, hollow body having a distal end, a proximal end and a central channel extending from aid proximal end to said distal end for removably receiving an optical catheter wherein the distal end of the catheter is alignable with said distal end of said body and a proximal end of the catheter is extendable outwardly beyond said proximal end of said body, the catheter being conformable to the shape and movement of said body;

an articulate hollow, cylindrical member within said sheath body at the distal end thereof extending along said sheath body for a short distance from said distal end;

a first pair of wires extending longitudinally within said sheath body from said distal end thereof to said proximal end thereof, each of said wires having a distal end connected on opposite sides of said distal end of said articulatable member; and first control means to simultaneously and alternatingly push one of said first pair of wires in the distal direction and pull the other of said first pair of wires to deflect said articulatable member and said distal end of said sheath body a flexible and removable non-steerable catheter having a longitudinal body having a distal end, said distal end of said catheter body being aligned with said distal end of said sheath so that said distal end of said catheter bends with said distal end of said sheath when said distal end of said sheath is deflected by said first control means;

a fiber bundle extending through said longitudinal body for providing light to the site; and an optic bundle extending through said longitudinal body for transmitting an image from the site to a viewing device.

3. Apparatus, as claimed in claim 2, further including:

a second pair of wires extending longitudinally within said sheath body from said distal end thereof to said proximal end thereof, each of said second pair of wires having a distal end connected on opposite sides of said distal end of said articulatable member and offset 90° from said first pair of wires; and a second control means to simultaneously and alternatingly push one of said second pair of wires in the distal direction and pull the other of said second pair of wires to deflect said articulatable member and said distal end of said sheath body 90° out of phase wit the deflection caused by said first pushing and pulling means.

* * * * *